(12) United States Patent
Kimata et al.

(10) Patent No.: US 6,387,646 B1
(45) Date of Patent: May 14, 2002

(54) REAGENT COMPOSITIONS FOR MEASURING ELECTROLYTE

(75) Inventors: Shinsuke Kimata; Katsuhiko Mizuguchi; Yoshihisa Kawamura, all of Tsuruga (JP)

(73) Assignee: Toyo Boseki Kabushiki Kaisha, Osaka (JP)

( * ) Notice: Subject to any disclaimer, the term of this patent is extended or adjusted under 35 U.S.C. 154(b) by 0 days.

(21) Appl. No.: 09/458,147

(22) Filed: Dec. 9, 1999

(30) Foreign Application Priority Data

Dec. 11, 1998 (JP) .......................... 10-353267

(51) Int. Cl.$^7$ .......................... C12Q 1/40; C12Q 1/00; G01N 33/53
(52) U.S. Cl. .................. 435/22; 435/963; 435/4
(58) Field of Search ................ 435/22, 4, 963

(56) References Cited

U.S. PATENT DOCUMENTS 5,229,270 A * 7/1993 Ono et al. ................ 435/22
5,470,715 A 11/1995 Mizuguchi et al. .......... 435/22

FOREIGN PATENT DOCUMENTS

| JP | 36199/1987 | 2/1987 |
| JP | 195297/1987 | 8/1987 |
| JP | 276597/1990 | 11/1990 |
| JP | 176000/1991 | 7/1991 |
| JP | 113894/1994 | 4/1994 |
| JP | 187296/1997 | 7/1997 |
| JP | 10014597 | * 1/1998 |

* cited by examiner

Primary Examiner—Louise N. Leary
(74) Attorney, Agent, or Firm—Leydig, Voit & Mayer, Ltd.

(57) ABSTRACT

The present invention provides a combination of reagent compositions for measuring an electrolyte which are excellent in stability, precision and quantitativity and have high solution stability sufficient to withstand distribution. In the combination of the reagent compositions of the present invention, a chelating agent and an inactivated α-amylase capable of being reversibly activated by the electrolyte are formulated separately from each other.

10 Claims, 1 Drawing Sheet

- Immediately after preparation
- After storage at 35°C for 14 days

- Immediately after preparation
- After storage at 35°C for 14 days

REAGENT COMPOSITIONS FOR MEASURING ELECTROLYTE

FIELD OF THE INVENTION

The present invention relates to reagent compositions for measuring electrolytes such as calcium ions and chloride ions in body fluids, in particular blood and urine. More specifically, the present invention relates to reagent compositions for measuring the electrolytes by utilizing α-amylases.

BACKGROUND OF THE INVENTION

Since the electrolyte level of the living body in the normal state is closely regulated by the metabolism, measurement of electrolyte level in body fluids is the most common biochemical clinical test for checking the function of the living body and diagnosing various diseases. For example, measurement of calcium ion level in serum is utilized for diagnosis of diseases involving hypocalcemia, such as hypoprotemia, hypophosphataemia, nephritis, nephrosis, vitamin D deficiency, hypoparathyroidism and rickets, and diseases involving hypercalcemia, such as bone tumors, Addison's disease, chronic pulmonary emphysema, hyperparathyroidism and renal failure. Further, measurement of chlorine ion level in serum is utilized for diagnosis of diseases involving hypochloremia, such as hypotonic dehydration, hyperglucocorticoidinemia and respiratory acidosis, and diseases involving hyperchloremia, such as hypertonic dehydration, renal tubular acidosis and respiratory alkalosis.

Known methods for measuring calcium ions in body fluids include (1) titration, (2) colorimetry, (3) atomic absorptiometry, (4) flame photometry, (5) electrode method, (6) enzyme method, etc.

The titration (1) is a chemical titration using oxalates or chelates. This method is disadvantageous in that it involves troublesome manipulations, causes operator-to-operator variation in measured value, and is incapable of treating a large amount of a sample in a short period of time. The colorimetry (2) utilizing o-CPC (orthocresolphthalein complexone) as the color developer can be performed with a general-purpose automatic analyzer, but this method is disadvantageous in that it involves temperature- or time-dependent variation in absorbance and is subject to the influence of magnesium ions.

The atomic absorptiometry (3) necessitates dilution of the sample and skilled manipulation to perform. The flame photometry (4) has problems with specificity and reproducibility. The electrode method (5) is disadvantageous in that it is subject to the influence of pH and necessitates apparatus that is difficult to maintain in constant conditions.

The enzyme method (6) includes (i) a method using phospholipase D (Japanese Unexamined Patent Publication No. 195297/1987), (ii) a method using calmodulin (Japanese Unexamined Patent Publication No. 36199/1987), (iii) a method using an α-amylase (Japanese Examined Patent Publication No. 87798/1994), etc.

The method (i) encounters difficulties in preparing a uniform substrate and requires much time for the reaction. The method (ii) necessitate 100- to 1000-fold dilution of the sample. On the other hand, the method (iii) is free from the problems of the above methods (1) to (5) and more precise and easier than the enzyme methods (i) and (ii), and thus has been put into practice in the field of clinical testing. The method (iii) is a method for measuring calcium ions in body fluids wherein an inactivated α-amylase is activated by calcium ions to decompose a sugar substrate, and the decomposition product is measured.

Conventional methods for measuring chlorine ions in body fluids include (A) coulometric titration, (B) ion electrode method, (C) colorimetry and (D) enzyme method. The coulometric titration (A) and ion electrode method (B) require a special apparatus, necessitate careful maintenance and control of the equipment, and have poor analysis efficiency. The colorimetry (C) includes a method using mercury thiocyanate and iron nitrate, which, however, produces waste liquid containing cyan or mercury and thus necessitates special waste liquid treatment, hence disadvantageous.

The enzyme method (D) includes (a) a method using an α-amylase (Japanese Unexamined Patent Publications Nos. 176000/1991, 94698/1992, etc.), (b) a method using sarcosine oxydase (Japanese Unexamined Patent Publication No. 187296/1987) and other methods. The method (a) is a method for measuring chlorine ions in body fluids, wherein an inactivated α-amylase is activated by chlorine ions to decompose a sugar substrate, and the decomposition product is measured. This method is superior in precision, handiness and analysis efficiency to the coulometric titration, ion electrode method and colorimetry, and thus has been put into practice in clinical testing.

In recent clinical testing, reagents are chiefly used in a solution form, for meeting the demand for improvement of precision and stability, cost reduction and labor saving. Conventionally, components unstable in a solution form, such as enzymes, are distributed as lyophilized, and are dissolved in the solvent packaged with the components, at the time of use. Recently, however, enzyme components have higher heat resistance, and can be improved in stability by optimizing pH and buffer conditions, and thus reagent compositions capable of being distributed in a solution form are available. The solution-form reagents are remarkably laborsaving in clinical testing, since it saves the manufacturer lyophilizing the reagents and the test operator dissolving the reagents.

As described above, the electrolyte measuring method utilizing an α-amylase is superior to various other conventional methods in handiness and precision. In this method, the α-amylase is usually inactivated in advance, by removing the target ions to be measured (such as calcium or chlorine ions) which are necessary for expression of the α-amylase activity. The reagents used in this method contain a chelating agent which inhibits a blank reaction, serves as an antagonist to control the quantitativity, and masks interfering ions analogous to the target ions. Since such an inactivated α-amylase is unstable in the presence of a chelating agent, the reagents have the problem that they cannot be stored in a solution form for a prolong period of time.

It is known that oligosaccharides such as maltose and α-cyclodextrin, and their mixtures are useful for stabilizing inactivated α-amylases in the presence of a chelating agent (Japanese Unexamined Patent Publication No. 113894/1994). However, the oligosaccharides are insufficient for stabilizing inactivated α-amylases for a long period of time or at room temperature (18 to 37° C.) at which the measurement is to be conducted, although they are useful for stabilization for a short period of time (1 to 2 months) at a low temperature (2 to 8° C.).

Further, the solution-form reagents may have the problem of admixture of α-amylases derived from outside the sample. For example, if human saliva is accidentally admixed into a solution-form reagent, α-amylases contained in the saliva decompose the substrate, so that the reagent blank increases and the measurement sensitivity reduces, resulting in lowered quantitativity and impaired precision. Foreign matters such as saliva are likely to be admixed at the time of production or use of reagents, and even a trace amount of sweat- or saliva-derived α-amylases, when admixed, affect the performance characteristics of reagents which may be stored in the form of a solution for a long period of time. Accordingly, α-amylases used in the solution-form reagents need to be stabilized.

In order to cope with the problem of admixed α-amylases derived from outside the sample, Japanese Unexamined Patent Publication No. 277096/1994 discloses a method wherein p-nitrophenyl-β-galactosyl-α-maltopentaoside for use as an α-amylase substrate is made into an aqueous solution at a pH of 2.0 to 5.5 for stabilization. This method can stabilize the α-amylase substrate, but is not sufficiently useful since it imposes limitations on the pH values of the reagent solutions.

As discussed above, although solution-form reagents are mainly used in clinical testing, no solution-form reagents have been developed so far which have sufficiently high solution stability to withstand distribution. Thus, the main object of the present invention is to provide reagent compositions for measuring an electrolyte, which enables enzymatic assay excellent in stability, precision and quantitativity.

SUMMARY OF THE INVENTION

The present inventors conducted extensive research to achieve the above object, and found that when the measurement is carried out using two reagent compositions wherein a chelating agent which may cause instability of α-amylases, and an inactivated α-amylase capable of being reversibly reactivated by an electrolyte are formulated separately from each other. The reagent compositions have, substantially without using stabilizers, long-term solution stability at low temperatures or at room temperature at which the reagent compositions are to be used. The present inventors further found that the influence of contaminating α-amylases can be suppressed by using a first reagent composition comprising at least (a) an α-amylase substrate and (b) a chelating agent, and a second reagent composition comprising (c) an inactivated α-amylase capable of being reversibly reactivated by an electrolyte, and the influence can be further reduced when the first reagent composition further contains (d) a substance having α-amylase inhibitory activity. The present invention has been accomplished based on these novel findings.

The present invention provides the following reagent compositions:
(1) A combination of reagent compositions for measuring an electrolyte by utilizing an α-amylase, wherein a chelating agent and an inactivated α-amylase capable of being reversibly reactivated by the electrolyte are formulated separately from each other.
(2) The combination according to Item (1) which comprises a first reagent composition comprising (a) an α-amylase substrate and (b) a chelating agent, and a second reagent composition comprising (c) an inactivated α-amylase capable of being reversibly reactivated by the electrolyte.
(3) The combination according to Item (2) wherein the first reagent composition further comprises a substance having α-amylase inhibitory activity.
(4) The combination according to Item (2) wherein the α-amylase substrate is 2-chloro-4-nitrophenyl-4-o-β-D-galactopyranosyl-α-maltoside.
(5) The combination according to Item (3) wherein the substance having α-amylase inhibitory activity is at least one member selected from the group consisting of 5-bromo-5-nitro-1,3-dioxane, 2-chloroacetamide, 2-hydroxypyridine-N-oxide, imidazolidinyl urea, N-methylisothiazolone, 5-chloro-2-methyl-4-isothiazolin-3-one and N-ethylmaleimide.
(6) The combination according to Item (1) wherein the chelating agent is 1,2-bis(o-aminophenoxy)ethane tetraacetic acid.
(7) The combination according to Item (2) wherein the first reagent composition has a pH of 7 or higher and the second reagent composition has a pH of 6 to 7.
(8) The combination according to Item (1) wherein the electrolyte is calcium ions.
(9) The combination according to Item (1) wherein the electrolyte is chlorine ions.

BRIEF DESCRIPTION OF DRAWINGS

In FIG. 1, the level of dilution is plotted on the x axis, and the measured calcium concentration (mg/dl) on the y axis.

In FIG. 2, the level of dilution is plotted on the x axis, and the measured calcium concentration (mg/dl) on the-y axis.

DETAILED DESCRIPTION OF THE INVENTION

Figure 1:
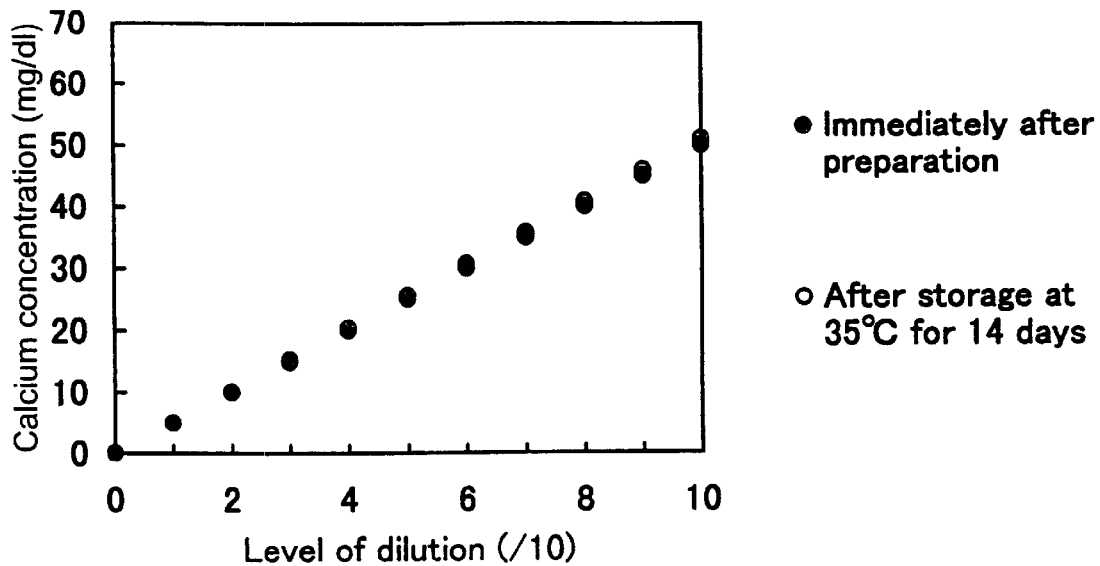
FIG. 1 is a graph showing the results of Example 2 wherein dilutions of aqueous calcium solution (50 mg/dl) having ten graded levels of dilution were subjected to measurement using the reagent compositions immediately after preparation and those stored at 35° C. for 14 days.

The reagent compositions of the present invention are used for measuring an electrolyte in a sample by utilizing a property of α-amylases, i.e., capability of being activated by ions such as calcium ions and chlorine ions. In the measurement using the reagent compositions of the invention, the amount of decomposed sugar substrate is measured to thereby find the concentration of an electrolyte in the sample, according to the following methods. As used herein, the term "electrolyte" is intended to mean a substance that, when dissolved in water or other medium, becomes an ionic conductor. Specific examples of electrolytes include calcium ions, chlorine ions, magnesium ions, barium ions, manganese ions and zinc ions.

(1) Method Utilizing a Maltooligosaccharide as the Substrate

In this method, glucose is released from the substrate such as maltotetraose, maltopentaose or maltohexaose by the action of an activated α-amylase and optionally a auxiliary enzyme such as α-glucosidase. Then, the released glucose is measured to find the concentration of the electrolyte such as calcium. The glucose can be measured by the glucose oxidase-peroxidase method, hexokinase-glucose-6-phosphate dehydrogenase method or like method.

The glucose oxidase-peroxidase method comprises allowing glucose oxidase to act on glucose, and converting the produced hydrogen peroxide into a quinone pigment by carrying out, in the presence of peroxidase, oxidation condensation with a coupler and a substance that develops color on oxidation (e.g., phenol), to thereby measure the rate of change in absorbance. The hexokinase-glucose-6-phosphate dehydrogenase method comprises converting glucose into glucose-6-phosphate using hexokinase, and allowing glucose-6-phosphate dehydrogenase to act on the glucose-6-phosphate in the presence of $NAD^+$ or $NADP^+$ to thereby measure the rate of increase of NADH or NADPH in the reaction.

(2) Method Utilizing as the Substrate a Maltooligosaccharide Derivative Having a Phenyl Group, Naphthyl Group or Derivative Thereof Bonded to its Reducing End as an Aglycon In this method, an activated α-amylase and optionally a auxiliary enzyme such as α-glucosidase are allowed to act on a substrate such as p-nitrophenylmaltopentaoside, p-nitrophenylmaltohexaoside, p-nitrophenylmaltopentaoside, 2,4-dichloronitrophenylmaltopentaoside 2-chloro-4-nitrophenylmaltotrioside or 2-chloro-4-nitrophenylmaltopentaoside, to release the aglycon from the substrate. The amount of the released aglycon is optically measured to determine the concentration of the electrolyte such as calcium.

(3) Method Utilizing as the Substrate a Maltooligosaccharide Derivative Having a Phenyl Group, Naphthyl Group or Derivative thereof Bonded to its Reducing End as an Aglycon, wherein the Hydroxyl Groups at the 4- and 6-Position of the Non-reducing End Glucose are Modified by Some Means This method is carried out according to method (2), using a substrate having a non-reducing end glucose modified by a halogen, glucopyranosyl or (as disclosed in Japanese Unexamined Patent Publication No. 237998/1985); a substrate having a non-reducing end glucose in which the hydroxyl groups at the 4- and 6-positions are substituted by alkyl, alkanoyl, or phenyl (as disclosed in Japanese Unexamined Patent Publications Nos. 54395/1985 and 157996/1989); or a substrate having a non-reducing end glucose in which the hydroxyl groups at the 4- and 6-positions are substituted by β-galactopyranosyl (as disclosed in Japanese Unexamined Patent Publications Nos. 264596/1991 and 315399/1994).

Among the above known methods, the method (3) is advantageous in principle. In particular, the method (3) using 2-chloro-4-nitrophenyl-4-o-β-D-galactopyranosyl-α-maltoside is advantageous in that the method is free from rise of the reagent blank since the non-reducing end of the substrate is modified to inhibit decomposition by endogenous a-glucosidase or the like, is inexpensive since it does not necessitate a auxiliary enzyme, and is highly sensitive owing to the high affinity of α-amylases to the substrate.

As one embodiment of the present invention, measurement of calcium ions will be described. First, the sample is reacted with a first reagent composition comprising a substance having α-amylase inhibitory activity, a chelating agent and 2-chloro-4-nitrophenyl-4-o-β-D-galactopyranosyl-α-maltoside as an α-amylase substrate (first reaction), and subsequently with a second reagent composition comprising an inactivated α-amylase capable of being reversibly reactivated by the electrolyte (second reaction), so that the α-amylase reactivated by calcium in the sample decomposes the substrate. Then, the released 2-chloro-4-nitrophenol is measured to find the calcium concentration in the sample.

In the present invention, the substance having α-amylase inhibitory activity is a substance that binds to a specific site of α-amylases to thereby decrease the reaction rate, in particular a substance having inhibitory activity other than competitive inhibition, such as a substance capable of reacting with or binding to a thiol group, amino group or other groups constituting proteins. Specific examples of such substances include, but are not limited to, 5-bromo-5-nitro-1,3-dioxane, 2-chloroacetamide, 2- hydroxypyridine-N-oxide, imidazolidinyl urea, N-methylisothiazolone, 5-chloro-2-methyl-4-isothiazoline-3-one, N-ethylmaleimide, p-chloromercury benzoate and β-bromoethylamine. These substances may be used singly or in combination. The concentration of the substance having α-amylase inhibitory activity is not limited but is preferably 0.01 to 100 mM in the first reagent composition, in view of the influence on the inactivated α-amylase contained in the reagent composition.

The α-amylase for use in the invention may be any of microbial, plant or animal origin. Preferable are α-amylases of animal origin, such as pig pancreatic α-amylases, human pancreatic α-amylases, and human salivary α-amylases. It is necessary that the α-amylase for use in the present invention be inactivated by desalting, and during the measurement, the α-amylase is reversibly reactivated by the electrolyte (e.g., calcium or chlorine ions) in the sample and reacts with the α-amylase substrate. The desalting can be carried out by, for example, dialysis, ultrafiltration, ion exchange, removal on a column, electromembrane dialysis, or like method. The concentration of the inactivated α-amylase in the reagent composition is such that the inactivated α-amylase in the reaction mixture becomes 0.1 to 1000 IU/ml.

According to the present invention, a specific species of ions in a sample containing several species of ions (such as blood or urine) can be measured by estimating the concentration range of the interfering ions (ions that activate the α-amylase but are not the target ions) and employing one of the following methods: (1) Use a chelating agent specific to the interfering ions in order to suppress activation of the α-amylase by the interfering ions; or (2) Add a sufficient amount of the interfering ions to the reagent composition prior to the measurement, so that the action of the target ions is not hindered by the interfering ions at the concentration in the sample.

Specifically stated, in the measurement of calcium ions, chlorine ions which may act as interfering ions, and thus a chlorine-containing compound such as NaCl is added to the reagent composition at a concentration such that the chlorine ions do not affect the measurement. Further, in the measurement of chlorine ions, a chelating agent for trapping calcium ions is added to the reagent composition, since chlorine ions may act as interfering ions.

Chelating agents usable in the invention include, for example, ethylenediamine tetraacetic acid, glycol ether diamine tetraacetic acid, 1,2-bis-(o-aminophenoxy)ethane tetraacetic acid, trans-1,2-diaminocyclohexane tetraacetic acid and their salts, among which 1,2-bis(o-amonophenoxy) ethane tetraacetic acid is particularly preferred from the viewpoint of the metal selectivity at neutral pHs, which are optimal in the present invention. The chelating agent in reagent compositions for measuring an electrolyte suppresses the blank reaction, serves as a competitive inhibitor to control the quantativity, and masks interfering ions analogous to the target ions. The chelating agent is used in an amount such that its concentration in the reaction mixture becomes preferably 0.01 to 10 mM, more preferably 0.1 to 1 mM. The chelating agents mentioned above may be used in combination.

As described above, the α-amylase substrate for use in the invention is not limited, but 2-chloro-4-nitrophenylmaltotrioside and 2-chloro-4-nitrophenyl-4-o-β-

D-galactopyranosylmaltoside are preferred since they do not necessitate a auxiliary enzyme, thus reducing the cost. In particular, 2-chloro-4-nitrophenyl-4-o-β-D-galactopyranosylmaltoside is particularly preferable for the following reasons: the substrate does not cause rise in the reagent blank since the non-reducing end of the substrate is modified to inhibit decomposition by endogenous a-glucosidase or the like; and the substrate can realize high sensitivity owing to the high affinity of α-amylase to the substrate. The substrate is contained in the reagent composition in an amount such that the concentration of the substrate in the reaction mixture becomes preferably 0.05 to 50 mM, more preferably about 0.1 to 2 mM.

According to the present invention, it is necessary to carry out the measurement by two steps, i.e., first and second reactions, using two reagent compositions wherein a chelating agent and an inactivated α-amylase capable of being reversibly reactivated by an electrolyte are formulated separately from each other. The inactivated α-amylase formulated separately from the chelating agent has a long-term solution stability. Further, when the reagent compositions are adjusted to a final pH of 5.0 to 8.0, the rate of sugar decomposition reaction of the α-amylase can be controlled, and thus broadening the range of measurement.

It is preferable that the reagent compositions according to the present invention is a combination of a first reagent composition comprising (a) an α-amylase substrate and (b) a chelating agent, and a second reagent composition comprising (c) an inactivated α-amylase capable of being reversibly reactivated by an electrolyte, in order to quickly attain, after addition of the second reagent composition, a zero-order reaction whose rate is measurable, and to facilitate preliminary treatment or elimination of interfering electrolytes. It is more preferable that the first reagent composition further contains (d) a substance having α-amylase inhibitory activity, for further reducing the influence of contaminating α-amylases.

The reagent compositions of the present invention preferably have a pH of 6 to 8, since the α-amylase is most stable at neutral pHs of 6 to 8 and the chelating agent is most stable at alkaline pHs. In order to achieve performance characteristics such as quantitativity as well as stability, each of the first and second reagent compositions are prepared so that the mixture of the two reagent compositions has a pH optimal for the reaction. It is preferable that the reagent composition comprising the chelating agent has a pH of 7 or higher, more preferably 7 to 9, and the reagent composition comprising the inactivated α-amylase has a pH of 6 to 7. Further, the buffer concentration and mixing ratio of the reagent compositions are adjusted to attain the pH optimal for the reaction.

The pH of the reagent compositions can be adjusted by any of known methods, usually using a buffer. Usable buffers include Good's buffer, Tris buffer and phosphate buffer. In each of the first and second reagent compositions, the buffer concentration is preferably 10 to 500 mM, more preferably 50 to 300 mM.

In order to suppress the reagent blank and improve the quantitativity, the compositions of the present invention may comprise a combination of two substrates which are measured by different optical methods, or a combination of a substrate and a product obtained therefrom to cause competitive sugar degradation reaction and thereby lower the apparent substrate affinity. In the "two substrates which are measured by different optical methods", one is a substrate as a mediator (herein referred to merely as "substrate") which causes the main reaction for measuring calcium ions. The other is a regulator substrate which can serve as an α-amylase substrate and competitively inhibits the main reaction to lower the apparent affinity of the amylase to the substrate causing the main reaction. The regulator substrate is used for suppressing the reagent blank and improving the quantitativity. For example, a regulator substrate selected from maltooligosaccharides, maltooligosaccharides having modified reducing end glucose, and maltooligosaccharides having a non-color-developing group bonded to the reducing end glucose, can be used as a competing substrate to control the rate of the main reaction of the α-amylase with the substrate having a color developing group bonded to the reducing end glucose, or a substrate having a color developing group bonded to the reducing end glucose and a substituent bonded to the non-reducing end glucose. In particular, maltooligosaccharides having modified non-reducing end glucose can be preferably used since it is not decomposed by α-glucosidase and thus exerts no influence on the measured value.

Examples of the above maltooligosaccharides include maltose, maltotriose, maltotetraose, maltopentaose, maltohexaose, maltoheptaose and like maltooligosacchrides having 2 to 7 glucose residues. Examples of maltooligosaccharides having a modified non-reducing end glucose include galactosyl maltose, galactosyl triose, galactosyl tetraose and galactosyl pentaose. Examples of maltooligosaccharides having a non-color-developing group bonded to the reducing end glucose include 2,4dichlorophenyl-α-D-maltotrioside, 2,4-dichlorophenyl-(α or β)-D-maltopentaoside and 2,4-dichlorophenyl-(α or β)-D-maltotrioside. The concentration of the maltooligosaccharide (regulator substrate) is preferably 0.01 to 250 mM, more preferably 0.1 to 200 mM in the reaction mixture. Either or both of the first and second reagent compositions may contain the maltooligosaccharides.

The reagent compositions of the present invention may further contain, where necessary, a binder, such as an ionophore or crown ether, selective to the interfering electrolytes or target electrolyte, for suppressing the influence of interfering electrolytes. Examples of selective binders include, in addition to the above mentioned chelating agents, 18-crown-6 and Kryptofix 221 (both manufacture by Merck Co., Ltd.). Further, the reagent compositions of the present invention may further contain an antiseptic, surfactant, antioxidant, protease inhibitor and other additives, on condition that they do not affect the quantitativity of the electrolyte measurement.

Useful antiseptics are not limited and include sodium azide and cephem, penicillin, aminoglycoside or quinolone antibiotics which have little influence on the stability of the α-amylase. These antiseptics may be used singly or in combination. Useful surfactants include nonionic surfactants, cationic surfactants and anionic surfactants. They can be used singly or in combination.

When the electrolyte to be measured is calcium ions, it is preferable to add an alkali metal halide such as sodium chloride or potassium chloride at a concentration of 3 to 300 mM. When the electrolyte to be measured is chlorine ions, a divalent cation such as calcium, magnesium, barium or zinc may be added at a concentration of 0.01 to 200 mM.

Usable antioxidants include ascorbic acid and its salts, sorbose and like saccharides, and catalases. Usable protease inhibitors include phenylmethylsulfonyl fluoride.

According to the present invention, an electrolyte in the sample can be measured by the following method, utilizing the inactivated α-amylase capable of being reversibly reactivated by the electrolyte (e.g., calcium or chlorine ions) in the sample to form an activated α-amylase which reacts with the α-amylase substrate. For example, calcium ions can be measured by reacting the sample with a first reagent composition comprising a substance having α-amylase inhibitory activity, a chelating agent and 2-chloro-4-nitrophenyl-4-o-β-D-galactopyranosyl-α-maltoside serving as an α-amylase substrate (first reaction), and then with a second reagent composition comprising an inactivated α-amylase capable of reversibly reactivated by the electrolyte, so that 2-chloro-4-nitrophenol is formed by the reaction of the a α-amylase reactivated by calcium ions in the sample.

Since 2-chloro-4-nitrophenol as such has an absorbance at about 400 nm, change in absorbance at about 400 nm after release is determined to find the calcium concentration in the sample, using the absorbance of a reference sample of a known concentration. The 2-chloro-4-nitrophenol can be determined by rate assay wherein the reaction of the α-amylase is continuously followed, or by the end point assay wherein the reaction is continued for a certain period of time and then stopped for measurement.

As another embodiment of the present invention, measurement of chlorine ions will be described. First, the sample is reacted with a first reagent composition comprising a substance having α-amylase inhibitory activity, a chelating agent and 2-chloro-4-nitrophenyl-4-o-β-D-galactopyranosyl-α-maltoside as an α-amylase substrate (first reaction), and then with a second reagent composition comprising an inactivated α-amylase capable of being reversibly reactivated by the electrolyte (second reaction). Subsequently, the amount of 2-chloro-4-nitrophenol produced by the reaction of the α-amylase reactivated by the chlorine ions in the sample is measured to find the chlorine ion concentration.

The following examples are provided to illustrate the invention and are not to limit the scope of the claims of the invention.

EXAMPLE 1

First and second reagent compositions of the following make-ups for measuring calcium were prepared, and the second reagent composition, which contained an α-amylase, was stored at 35° C. for 14 days. The α-amylase activity of the second reagent composition was determined immediately after preparation, and 5, 10 and 14 days after preparation, using a commercially available reagent for measuring α-amylase activity (Diacolor AMY Neorate manufactured by Toyobo Co., Ltd.) to find the remaining activity (%). The results are shown in Table 1.

| (1) First reagent composition | |
|---|---|
| Tris-hydrochloric acid buffer (pH 7.1) | 50 mM |
| NaCl | 200 mM |
| 1,2-bis(o-aminophenoxy)ethane tetraacetic acid | 0.8 mM |
| Galactosylmaltose | 2.3 mM |
| Polyoxyethyleneoctylphenyl ether | 0.05% |
| 2-Chloro-4-nitrophenyl-4-o-β-D-galactopyranosyl-α-maltoside | 0.9 mM |
| (2) Second reagent composition | |
| Good's buffer (pH 6.0) | 300 mM |
| NaCl | 200 mM |
| Galactosylmaltose | 2.3 mM |
| Polyoxyethyleneoctylphenyl ether | 0.05% |
| Inactivated α-amylase (pig pancreas-derived) | 4.2 IU/ml |

Comparative Example 1

First and second reagent compositions of the following make-ups for measuring calcium were prepared, and the first reagent composition, which contained an α-amylase, was stored at 35° C. for 14 days. The remaining activity (%) was determined in the same manner as in Example 1. The results are shown in Table 1.

| (1) First reagent composition | |
|---|---|
| Tris-hydrochloric acid buffer (pH 7.1) | 50 mM |
| 1,2-bis(o-aminophenoxy)ethane tetraacetic acid | 0.8 mM |
| Galactosyl maltose | 2.3 mM |
| Polyoxyethyleneoctylphenyl ether | 0.05% |
| NaCl | 200 mM |
| Inactivated α-amylase (pig pancreas-derived) | 2.1 IU/ml |
| (2) Second reagent composition | |
| Good's buffer (pH 6.0) | 300 mM |
| NaCl | 200 mM |
| Galactosylmaltose | 2.3 mM |
| Polyoxyethyleneoctylphenyl ether | 0.05% |
| 2-Chloro-4-nitrophenyl-4-o-β-D-galactopyranosyl-α-maltoside | 1.8 mM |

TABLE 1

| | Remaining activity (%) | | | |
|---|---|---|---|---|
| Storage Period (day) | 0 | 5 | 10 | 14 |
| Example 1 | 100.0 | 97.7 | 96.3 | 97.2 |
| Comparative Example 1 | 100.0 | 72.0 | 51.8 | 39.4 |

Table 1 shows that, while the remaining α-amylase activity in Comparative Example 1 was only 39.4%, the remaining α-amylase activity in Example 1 was 97.2%, i.e., the α-amylase used in Example 1 suffered substantially no deterioration and had good stability.

EXAMPLE 2

The same first and second reagent compositions for measuring calcium as in Example 1 were prepared, and stored at 35° C. for 14 days. Using the reagent compositions immediately after preparation and those after storage, the calcium concentration in samples were measured to determine the linearity at high concentrations. The samples used were purified water, a standard solution having a calcium concentration of 10 mg/dl, and dilutions of aqueous calcium acetate solution (Ca ion concentration: 50 mg/dl) having ten graded levels of dilution.

Method for Measuring Calcium

180 μl of the first reagent composition was added to 3.5 μl of the sample, followed by 5-minute preliminary heating. Then, 90 μl of the second reagent composition was added to initiate the reaction. The absorbance change per minute was determined during the 3-minute period starting from 2 minutes after addition of the substrate-containing reagent composition, to thereby find the calcium concentration in the sample, using two calibration curves of the purified water and 10 mg/dl standard solution. The measurement was carried out using Hitachi Autoanalyzer 7170 at a dominant wavelength of 405 nm and a secondary wavelength of 546 nm, at a measuring temperature of 37° C.

Comparative Example 2

The same first and second reagent compositions for measuring calcium as in Comparative Example 1 were prepared, and stored at 35° C. for 14 days. Using the reagent compositions immediately after preparation and those after storage, the linearity at high concentrations was determined in the same manner as in Example 2.

Figure 2:
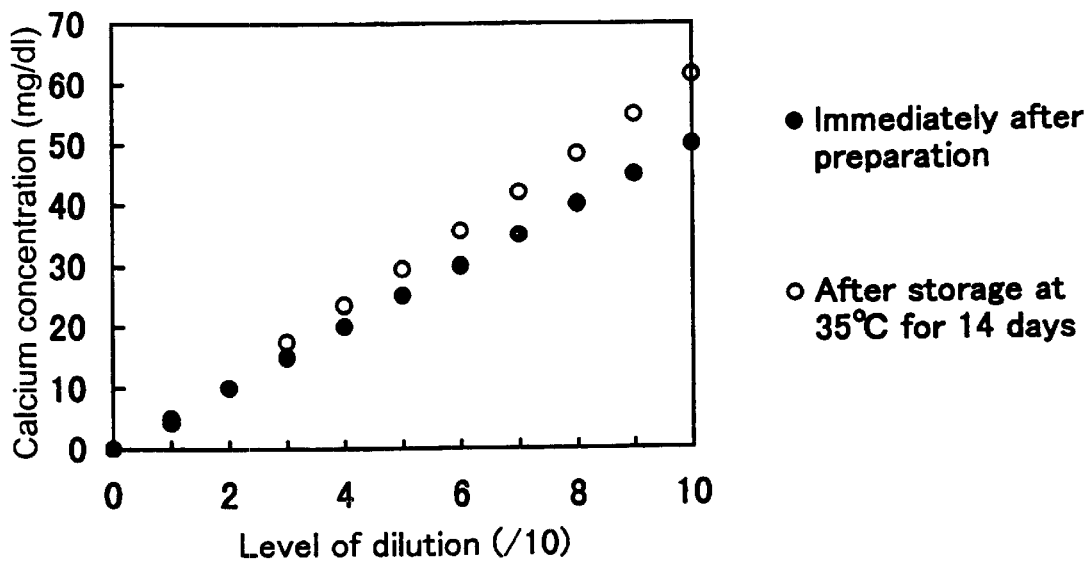
FIG. 2 is a graph showing the results of Comparative Example 2 wherein dilutions of aqueous calcium solution (50 mg/dl) having ten graded levels of dilution were subjected to measurement using the reagent compositions immediately after preparation and those stored at 35° C. for 14 days.

In FIGS. 1 and 2, the curve obtained in Comparative Example 2 is significantly warped at high concentrations, whereas the curve obtained in Example 2 has high linearity with substantially no warpage, showing that the reagent compositions of Example 2 are highly stable.

EXAMPLE 3

Eight combinations of first and second reagent compositions for measuring calcium were prepared, seven of which had the following make-ups wherein the substance having α-amylase inhibitory activity was (a) 5-bromo-5-nitro-1,3-dioxane, (b) 2-chloroacetamide, (c) 2-hydroxypyridine-N-oxide, (d) imidazolydinyl urea, (e) N-methylisothiazolone, (f) 5-chloro-2-methyl-4-isothiazoline-3-one or (g) N-ethylmaleimide. The other combination of the first and second reagent compositions had the following make-ups except that (h) no substance having α-amylase inhibitory activity was used. A human salivary α-amylase was admixed to each of the reagent compositions at a concentration of 3 IU/L. The resulting reagent compositions were stored at 35° C. for 14 days. The same reagent compositions which did not contain the human salivary α-amylase were stored in the same manner. Using these reagent compositions and purified water as the sample, the method for measuring calcium described in Example 2 was carried out to determine the initial absorbance (the absorbance at the starting point of the photometry of the purified water) of the reagent compositions immediately after preparation and 5, 10 and 14 days after preparation. The results are shown in Table 2.

(1) First reagent composition

| | |
|---|---|
| Tris-hydrochloric acid buffer (pH 7.1) | 50 mM |
| NaCl | 200 mM |
| 1,2-bis(o-aminohenoxy)ethane tetraacetic acid | 0.8 mM |
| Galactosyl maltose | 2.3 mM |
| Polyoxyethyleneoctylphenyl ether | 0.05% |
| 2-Chloro-4-nitrophenyl-4-o-β-D-galactopyranosyl-α-maltoside | 0.9 mM |
| Substance having α-amylase inhibitory activity | 0.05% |

(2) Second reagent composition

| | |
|---|---|
| Good's buffer (pH 6.0) | 300 mM |
| NaCl | 200 mM |
| Galactosyl maltose | 2.3 mM |
| Polyoxyethyleneoctylphenyl ether | 0.05% |
| Inactivated α-amylase (pig pancreas-derived) | 4.2 IU/ml |

Comparative Example 3

The same first and second reagent compositions for measuring calcium as in Comparative Example 1 were prepared. Using the obtained reagent compositions and the same sample as in Example 3, calcium measurement was carried out in the same manner as in Example 3 to determine the initial absorbance of the reagent compositions immediately after preparation and 5, 10 and 14 days after preparation. The results are shown in Table 2.

TABLE 2

| | | Initial Absorbance | | | |
|---|---|---|---|---|---|
| Storage Period (day) | | 0 | 5 | 10 | 14 |
| Ex. 3-(a) | Without salivary α-amylase | 42.7 | 38.9 | 38.4 | 39.7 |
| | With salivary α-amylase | 42.2 | 40.9 | 40.1 | 40.1 |
| | Δ | −0.6 | 2.0 | 1.8 | 0.4 |
| Ex. 3-(b) | Without salivary α-amylase | 39.4 | 38.8 | 37.2 | 36.6 |
| | With salivary α-amylase | 39.5 | 42.5 | 44.3 | 46.5 |
| | Δ | 0.1 | 3.7 | 7.1 | 9.9 |
| Ex. 3-(c) | Without salivary α-amylase | 38.8 | 39.2 | 38.9 | 37.9 |
| | With salivary α-amylase | 39.8 | 54.0 | 69.9 | 82.8 |
| | Δ | 1.0 | 14.8 | 31.0 | 44.9 |
| Ex. 3-(d) | Without salivary α-amylase | 39.4 | 38.4 | 38.6 | 37.2 |
| | With salivary α-amylase | 38.6 | 51.2 | 63.6 | 71.0 |
| | Δ | −0.8 | 12.8 | 25.0 | 33.8 |
| Ex. 3-(e) | Without salivary α-amylase | 38.4 | 33.6 | 33.3 | 34.4 |
| | With salivary α-amylase | 38.9 | 41.3 | 44.0 | 45.8 |
| | Δ | 0.5 | 7.7 | 10.8 | 11.4 |
| Ex. 3-(f) | Without salivary α-amylase | 42.3 | 40.0 | 38.9 | 40.0 |
| | With salivary α-amylase | 43.0 | 42.0 | 38.6 | 40.5 |
| | Δ | 0.7 | 2.0 | −0.3 | 0.5 |
| Ex. 3-(g) | Without salivary α-amylase | 40.5 | 37.1 | 37.1 | 36.2 |
| | With salivary α-amylase | 41.8 | 40.5 | 40.6 | 41.0 |
| | Δ | 1.3 | 3.4 | 3.5 | 4.8 |
| Ex. 3-(h) | Without salivary α-amylase | 39.0 | 33.8 | 32.2 | 33.8 |
| | With salivary α-amylase | 39.2 | 56.5 | 72.2 | 95.5 |
| | Δ | 0.2 | 22.7 | 40.0 | 61.7 |
| Comp. Ex. 3 | Without salivary α-amylase | 30.3 | 26.8 | 27.2 | 26.5 |
| | With salivary α-amylase | 39.2 | 395.5 | 722.7 | 858.7 |
| | Δ | 9.2 | 368.7 | 695.6 | 832.2 |
| | | | | | (mABS) |

Table 2 shows that, in Comparative Example 3, the initial absorbance of the reagent compositions containing the salivary α-amylase was significantly higher than that of the reagent compositions without the salivary α-amylase, whereas in Example 3, the increase of the initial absorbance of the reagent compositions was suppressed. In particular, when the first reagent composition contains a substance having α-amylase inhibitory activity, the increase of the initial absorbance was significantly suppressed.

EXAMPLE 4

First and second compositions of the following make-ups for measuring calcium were prepared, and stored at 40° C. Using the reagent compositions immediately after preparation and after 1, 4 and 7 days after preparation, calcium measurement was carried out in the same manner as in Example 2. Samples used were purified water, a standard solution with a calcium concentration of 10 mg/dl and commercial control serums "Monitrol IX" and "Monitrol IIX". Then, the change with time lapse in sensitivity to the 10 mg/dl standard solution and in measured calcium concentration in the serums was determined as the percentage relative to the values obtained using the reagent compositions immediately after preparation. The results are shown in Tables 3 and 4.

(1) First reagent composition

| | |
|---|---|
| Tris-hydrochloric acid buffer (pH 7.1) | 50 mM |
| NaCl | 200 mM |
| 1,2-bis(o-aminohenoxy)ethane tetraacetic acid | 0.8 mM |
| Galactosyl maltose | 2.3 mM |
| Polyoxyethyleneoctylphenyl ether | 0.05% |
| 2-Hydroxypyridine-N-oxide | 0.05% |
| 2-Chloro-4-nitrophenyl-4-o-β-D-galactopyranosyl-α- | 0.9 mM |

-continued

| | |
|---|---|
| maltoside | |
| (2) Second reagent composition | |
| Good's buffer (pH 6.5) | 300 mM |
| NaCl | 200 mM |
| Polyoxyethyleneoctylphenyl ether | 0.05% |
| Inactivated α-amylase (pig pancreas-derived) | 4.2 IU/ml |

Comparative Example 4

The procedure of Example 4 was repeated using first and second reagent compositions of the following make-ups for measuring calcium. The results are shown in Tables 3 and 4.

| | |
|---|---|
| (1) First reagent composition | |
| Tris-hydrochloric acid buffer (pH 7.1) | 50 mM |
| NaCl | 200 mM |
| 1,2-bis(o-aminophenoxy)ethane tetraacetic acid | 0.8 mM |
| Galactosyl maltose | 2.3 mM |
| Polyoxyethyleneoctylphenyl ether | 0.05% |
| 2-Hydroxypyridine-N-oxide | 0.05% |
| Inactivated α-amylase (pig pancreas-derived) | 2.1 IU/ml |
| (2) Second reagent composition | |
| Good's buffer (pH 6.0) | 300 mM |
| NaCl | 200 mM |
| Polyoxyethyleneoctylphenyl ether | 0.05% |
| 2-Chloro-4-nitrophenyl-4-o-β-D-galactopyranosyl-α-maltoside | 1.8 IU/ml |

EXAMPLE 5

The procedure of Example 4 was followed using first and second reagent compositions of the following make-ups for measuring calcium. The results are shown in Tables 3 and 4.

| | |
|---|---|
| (1) First reagent composition | |
| Tris-hydrochloric acid buffer (pH 7.1) | 50 mM |
| NaCl | 200 mM |
| 1,2-bis(o-aminophenoxy)ethane tetraacetic acid | 0.8 mM |
| Galactosyl maltose | 2.3 mM |
| Polyoxyethyleneoctylphenyl ether | 0.05% |
| 2-Hydroxypyridine-N-oxide | 0.05% |
| 2-chloro-4-nitrophenyl-4-o-β-D-galactopyranosyl-α-maltoside | 0.9 mM |
| (2) Second reagent composition | |
| Good's buffer (pH 6.5) | 300 mM |
| NaCl | 200 mM |
| Polyoxyethyleneoctylphenyl ether | 0.05% |
| Inactivated α-amylase (human saliva-derived) | 12 IU/ml |

Comparative Example 5

The procedure of Example 4 was followed using first and second reagent compositions of the following make-ups for measuring calcium. The results are shown in Tables 3 and 4.

| | |
|---|---|
| (1) First reagent composition | |
| Tris-hydrochloric acid buffer (pH 7.1) | 50 mM |
| NaCl | 200 mM |
| 1,2-bis(o-aminophenoxy)ethane tetraacetic acid | 0.8 mM |
| Galactosyl maltose | 2.3 mM |
| Polyoxyethyleneoctylphenyl ether | 0.05% |
| 2-Hydroxypyridine-N-oxide | 0.05% |
| Inactivated α-amylase (human saliva-derived) | 6 IU/ml |
| (2) Second reagent composition | |
| Good's buffer (pH 6.5) | 300 mM |
| NaCl | 200 mM |
| Polyoxyethyleneoctylphenyl ether | 0.05% |
| 2-Chloro-4-nitrophenyl-4-o-β-D-galactopyranosyl-α-maltoside | 1.8 IU/ml |

TABLE 3

| | Relative sensitivity (%) | | | |
|---|---|---|---|---|
| Storage period (day) | 0 | 1 | 4 | 7 |
| Ex. 4 | 100 | 75 | 51 | 43 |
| Ex. 5 | 100 | 99 | 99 | 95 |
| Comp. Ex. 4 | 100 | 79 | 44 | 28 |
| Comp. Ex. 5 | 100 | 91 | 64 | 51 |

TABLE 4

| | Relative measured calcium concentration in serums (%) | | | | |
|---|---|---|---|---|---|
| Storage period (day) | | 0 | 1 | 4 | 7 |
| Ex. 4 | Monitrol IX | 100 | 101 | 100 | 100 |
| | Monitrol IIX | 100 | 99 | 99 | 102 |
| Ex. 5 | Monitrol IX | 100 | 100 | 102 | 100 |
| | Monitrol IIX | 100 | 99 | 101 | 100 |
| Comp. Ex. 4 | Monitrol IX | 100 | 99 | 94 | 91 |
| | Monitrol IIX | 100 | 118 | 135 | 144 |
| Comp. Ex. 5 | Monitrol IX | 100 | 98 | 99 | 95 |
| | Monitrol IIX | 100 | 106 | 112 | 114 |

Table 3 shows that the reduction in sensitivity to the 10 mg/dl standard solution was smaller in Examples 4 and 5, as compared with Comparative Examples 4 and 5, respectively. Further, comparing the results of Example 4 with those of Example 5, it is revealed the reagent compositions prepared using a human saliva-derived α-amylase show less reduction in sensitivity and have higher storage stability than those prepared using a pig pancreas-derived α-amylase.

Table 4 shows that there was no change in the measured calcium concentration in the serums with time lapse in Examples 4 and 5, whereas in Comparative Examples 4 and 5, the measured calcium concentration in Monitrol IX decreased and that of Monitrol IIX increased with time lapse.

As described above, the reagent compositions for measuring an electrolyte according to the present invention are a combination of reagent compositions wherein a chelating agent that may impair the stability and an inactivated α-amylase capable of being reversibly reactivated are formulated separately from each other. As the result, the reagent compositions of the present invention have, substantially without using stabilizers, long-term solution stability, at low temperatures and at room temperature at which the reagent compositions are to be used. Further, when the reagent compositions of the invention are a combination of a first reagent composition comprising at least (a) an α-amylase substrate and (b) a chelating agent, and a second reagent composition comprising (c) an inactivated α-amylase capable of being reversibly reactivated by an electrolyte, the influence of admixed α-amylase can be suppressed. In particular, when the first reagent composition further contains (d) a substance having α-amylase inhibitory activity, the influence can be further reduced. Accordingly, the reagent compositions for measuring an electrolyte of the present invention are excellent in stability, precision and quantitativity.

What is claimed is:

1. A reagent composition kit, for measuring an electrolyte utilizing an α-amylase, comprising a chelating agent and an inactivated α-amylase capable of being reversibly reactivated by the electrolyte, wherein the chelating agent and the inactivated α-amylase are separate from each other in the kit.

2. The reagent composition kit according to claim 1, which comprises a first reagent composition comprising (a) an α-amylase substrate and (b) a chelating agent, and a second reagent composition comprising (c) an inactivated α-amylase capable of being reversibly reactivated by the electrolyte.

3. The reagent composition kit according to claim 2, wherein the first reagent composition further comprises (d) a substance having α-amylase inhibitory activity.

4. The reagent composition kit according to claim 2 wherein the α-amylase substrate is 2-chloro-4-nitrophenyl-4-o-β-D-galactopyranosyl-α-maltoside.

5. The reagent composition kit according to claim 3 wherein the substance having α-amylase inhibitory activity is at least one member selected from the group consisting of 5-bromo-5-nitro-1,3-dioxane, 2-chloroacetamide, 2-hydroxypyridine-N-oxide, imidazolidinyl urea, N-methylisothiazolone, 5-chloro-2-methyl-4-isothiazolin-3-one and N-ethylmaleimide.

6. The reagent composition kit according to claim 1 wherein the chelating agent is 1,2-bis(o-aminophenoxy) ethane tetraacetic acid.

7. The reagent composition kit according to claim 2 wherein the first reagent composition has a pH of 7 or higher and the second reagent composition has a pH of 6 to 7.

8. The reagent composition kit according to claim 1 wherein the electrolyte is calcium ions.

9. The reagent composition kit according to claim 1 wherein the electrolyte is chlorine ions.

10. A method for measuring an electrolyte comprising (a) providing the reagent composition kit of claim 1, (b) providing an α-amylase substrate, (c) reacting the chelating agent and the α-amylase substrate with a sample, (d) reacting the inactivated α-amylase with the sample, and (e) measuring the electrolyte of the sample.

* * * * *